(12) United States Patent
Kriegler et al.

(10) Patent No.: US 7,795,227 B2
(45) Date of Patent: *Sep. 14, 2010

(54) COMPOUNDS AND METHODS FOR TREATING SEIZURE DISORDERS

(75) Inventors: Steven M. Kriegler, Madison, WI (US); Avtar S. Roopra, Madison, WI (US); Thomas P. Sutula, Madison, WI (US); Carl E. Stafstrom, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/155,200

(22) Filed: Jun. 17, 2005

(65) Prior Publication Data

US 2006/0088517 A1  Apr. 27, 2006

Related U.S. Application Data

(60) Provisional application No. 60/580,436, filed on Jun. 17, 2004.

(51) Int. Cl.
*A61K 31/70* (2006.01)
(52) U.S. Cl. ....................................................... 514/23
(58) Field of Classification Search ................... 514/23
See application file for complete search history.

(56) References Cited

U.S. PATENT DOCUMENTS

| | | | |
|---|---|---|---|
| 5,643,883 A | 7/1997 | Marchase | |
| 6,620,850 B2 | 9/2003 | Martynyuk et al. | |
| 6,670,330 B1 | 12/2003 | Lampidis | |
| 6,979,675 B2* | 12/2005 | Tidmarsh | 514/23 |
| 6,989,400 B2 | 1/2006 | Tidmarsh | |
| 7,145,032 B2* | 12/2006 | Dugan et al. | 560/127 |
| 7,160,865 B2 | 1/2007 | Lampidis et al. | |
| 2003/0055099 A1 | 3/2003 | Martynyuk | |
| 2003/0181393 A1 | 9/2003 | Lampidis | |
| 2003/0216472 A1 | 11/2003 | Martynyuk | |
| 2004/0147590 A1 | 7/2004 | Martynyuk | |
| 2004/0167079 A1 | 8/2004 | Tidmarsh | |
| 2004/0167196 A1 | 8/2004 | Tidmarsh | |
| 2004/0266851 A1 | 12/2004 | Martynyuk | |
| 2005/0043250 A1 | 2/2005 | Lampidis | |
| 2005/0245462 A1 | 11/2005 | Tidmarsh | |
| 2005/0271723 A1 | 12/2005 | Tidmarsh | |
| 2005/0272795 A1 | 12/2005 | Tidmarsh | |
| 2005/0272796 A1 | 12/2005 | Tidmarsh | |
| 2006/0025351 A1 | 2/2006 | Lampidis | |
| 2006/0088517 A1 | 4/2006 | Kriegler | |
| 2006/0172953 A1 | 8/2006 | Tidmarsh | |
| 2006/0205649 A1 | 9/2006 | Roopra | |
| 2006/0217303 A1 | 9/2006 | Kriegler | |
| 2006/0287253 A1 | 12/2006 | Kriegler | |

2007/0088074 A1  4/2007  Martynyuk

FOREIGN PATENT DOCUMENTS

| | | |
|---|---|---|
| AU | 4006701 A | 11/2001 |
| AU | 2004206869 | 8/2004 |
| AU | 2004206870 | 8/2004 |
| AU | 2004204778 | 7/2005 |
| AU | 2005258021 | 11/2007 |
| BR | 0406667 A | 12/2005 |
| BR | 0406796 A | 7/2006 |
| CA | 2411406 A1 | 8/2001 |
| CA | 2513399 A1 | 7/2004 |
| CA | 2513572 A1 | 8/2004 |
| CA | 2513575 A1 | 8/2004 |
| CA | 2571055 | 1/2006 |
| CN | 1972697 A | 1/2006 |
| CN | 1771043 A | 2/2006 |
| EP | 1322304 A1 | 7/2003 |
| EP | 1446111 A1 | 8/2004 |
| EP | 1587519 A2 | 6/2005 |
| EP | 1592430 A2 | 11/2005 |
| EP | 1610778 A2 | 1/2006 |
| EP | 1789023 A2 | 5/2007 |
| EP | 1789030 A2 | 5/2007 |
| EP | 1789107 A2 | 5/2007 |
| EP | 4702967 | 8/2007 |
| ES | 2254046 T1 | 6/2006 |
| JP | 2006515883 T2 | 6/2006 |
| JP | 2006516571 T2 | 7/2006 |
| JP | 2006518343 T2 | 8/2006 |
| KR | 20050098244 A | 10/2005 |
| KR | 20050098249 A | 10/2005 |
| KR | 20050098250 A | 10/2005 |
| MX | PA05007382 A | 11/2005 |
| MX | PA05007571 A | 11/2005 |
| MX | PA05007572 A | 11/2005 |

(Continued)

OTHER PUBLICATIONS

Combs et al., Stroke, vol. 17, pp. 989-994, 1986.*
Ballaban-Gil et al., "Complications of the Ketogenic Diet," Elilepsia 39(7)744-48 (1998).
Bollinger et al., "Derivate der 2-Desoxy-aldehydo-D-glucose," Fasciculus III 119:989-991 (1951).
Bough et al., "Path Analysis Shows That Increasing Ketogenic Ratio, but Not B-Hydroxybutyrate, Elevates Seizure Threshold in the Rat," Dev. Neurosci 21:400-6 (1999).
Cavazos et al., "Mossy Fiber Synaptic Reorganization Induced by Kindling: Time Course of Development, Progression, and Permanence," Journ. of Neurosci. 11(9)2795-03 (1991).
Freeman et al., "The Efficacy of the Ketogenic Diet-1998: A Prospective Evaluation of Intervention in 150 Children" Pediatrics 6(102)1358-63 (1998).

(Continued)

*Primary Examiner*—Elli Peselev
(74) *Attorney, Agent, or Firm*—McDonnell Boehnen Hulbert & Berghoff

(57) ABSTRACT

This invention provides methods for alleviating paroxysmal disorders in an animal, particularly epilepsy, by modulating glycolysis in brain cells.

28 Claims, 12 Drawing Sheets

FOREIGN PATENT DOCUMENTS

| | | |
|---|---|---|
| NO | 20053782 A | 9/2005 |
| NO | 20053783 A | 9/2005 |
| RU | 2005126042 A | 2/2006 |
| RU | 2005125428 A | 3/2006 |
| WO | WO 01/82926 A1 | 11/2001 |
| WO | WO 03/024443 A1 | 3/2003 |
| WO | WO 2004/062604 A2 | 7/2004 |
| WO | WO 2004/064736 A3 | 8/2004 |
| WO | WO 2006/002121 A2 | 1/2006 |
| WO | WO 2006/024488 A2 | 3/2006 |
| WO | WO 2006/024489 A2 | 3/2006 |
| WO | WO 2006/024490 A2 | 3/2006 |
| WO | WO 2006/024491 A1 | 3/2006 |
| WO | WO 2006/024492 A3 | 3/2006 |
| WO | WO 2006/088849 A1 | 8/2006 |
| WO | WO 2006/105019 A1 | 10/2006 |

OTHER PUBLICATIONS

Goddard et al., "A Permanent Change in Brain Function Resulting from Daily Electrical Stimulation," Experimental Neurology 25:295-330 (1969).

Kaplan et al., "Effects of 2-Deoxyglucose on Drug-sensitive and Drug-resistant Human Breast Cancer Cells: Toxicity and Magnetic Resonance Spectroscopy Studies of Metabolism," Cancer Research 50:544-51 (Feb. 1, 1990).

McNamara et al., "Emerging insights into the genesis of epilepsy," Nature 399:A15-A22 (Jun. 24, 1999).

Morrell et al., "Kindling in the Frog: Development of Spontaneous Epileptiform Activity," Electroencephalography and Clinical Neurophysiology 40:1-11 (1976).

Oravcova et al., "Drug-protein binding studies New trends in analytical and experimental methodology," Journal of Chromatography 677:1-28(1996).

Rho et al., "The Pharmacologic Basis of Antiepileptic Drug Action," Epilepsia 40(11)1471-83 (1999).

Sayin et al., "Spontaneous Seizures and Loss of Axo-Axonic and Axo-Somatic Inhibition Induced by Repeated Breif Seizures in Kindled Rats," Journal of Neuroscience 23(7)2759-68 (Apr. 1, 2003).

Sowden et al., "Carbohydrate C-Nitroalcohols: the Acetylated Nitroolefins," JACS 69:1048-50 (1947).

Stafstrom et al., "The Pathophysiology of Epileptic Seizures: A Primer for Pediatricians," Pediatrics in Review 19 (10)342-51 (1998).

Sutula et al., "Quantitative Analysis of Synaptic Potentiation During Kidling of the Perforant Path," Journal of Neurophysiology 56(3)732-46 (1986).

Wada et al., "Limbic Kindling in the Forebrain-Bisected Photsensitive Baboon, *Papio papio*," Epilepsia 25(3):278-87 (1984).

Wada et al., "Recurrent Spontaneous Seizure State Induced by Prefrontal Kindling in Senegalese Baboons, *Papio papio*," Canadian Journal of Neurological Sciences 2:477-92 (1975).

Bergmann et al., "Berichte Der Deutchen Chemischen Gesellschaft" Berlin 55:158-173 (1922).

Rejdak et al., "2-deoxyglucose enhances epileptic tolerance evoked by transient incomplete brain ischemia in mice," Epilepsy Research 43(3):271-78 (Mar. 2001).

Lee et al., "2-deoxy-D-glucose protects hippocampal neurons against excitotoxic and oxidative injury: evidence for the involvement of stress proteins," Journ. of Neuro. Research 57(1)48-61 (1999).

Zhi et al., In vivo 2-deoxyglucose administration preserves glucose and glutamate transport and mitochondrial function in cortical synaptic terminals after exposure to amyloid "betal!-peptide and iron: Evidence for a stress response," Experimental Neurology 166(1)173-179 (2000).

Duan et al., "Dietary restriction and 2-deoxyglucose administration improve behavioral outcome and reduce degeneration of dopaminergic neurons in models of Parkinson's disease," Journ. of Neuro. Research 57(2)195-206 (1999).

Bodnar et al., "2-Deoxy-D-glucose analgesia: influences of opiate and non-opiate factors," Pharmacology, Biochemistry and Behavior11(3)297-301 (1979).

Fisher et al. "2-Deoxy-D-glucose antinociception and serotonin receptor subtype antagonist: test-specific effects in rats," Pharmacology, Biochemistry, and Behavior 43(4)1241-46 (1992).

Bodnar et al., "Capsaicin treatment and stress-induced analgesia," Pharmacology, Biochemistry and Behavior 18(1) 65-71 (1983).

Bodnar et al., "Neuropharmacological and neuroendocrine substrates of stress-induced pain modulation," Annals of the NY Acad. of Sci. 467:345-60 (1986).

Mukherjee et al., "Ventromedial hypothalamic mediation of sucrose feeding induced pain modulation," Pharmacology, Biochemistry and Behavior 68(1)43-38 (Jan. 2001).

Mireia Garriga-Canut et al., 1996, 2-Deoxy-D-glucose reduces epilepsy progression by NRSF-CtBP-dependent metabolic regulation of chromatin structure, Nature Neurosci 9(11): 1382-7.

Sayyah et al., 2005, "Anti-epileptogenic effect of β-carotene and vitamin A in pentylenetetrazole-kindling model of epilepsy in mice," Epilepsy Research 63: 11-16.

Vittorelli et al., 2005, "Characteristics of glutamine metabolism in human precision-cut kidney slices: a $^{13}$C-NMR study," Biochem J 387: 825-834.

Lan et al., 2008, "Neuronal Peroxisome Proliferator-Activated Receptor γ Signaling: Regulation by Mood-Stabilizer Valproate," J Mol Neurosci 35:225-234.

Okada et al., 2006 "Ameliorative effect of pioglitazone on seizure responses in genetically epilepsy-susceptible EL mice," Brain Research 1102:175-178.

Green et al., "Caloric Restriction Inhibits Seizure Susceptibility in Epilpetic EL Mice by Reducing Blood Glucose," Epilepsia 42(11):1371-1378 (2001).

Lian et al., "Fructose-1, 6-Bisphosphate Has Anticonvulsant Activity in Models of Acute Seizures in Adult Rats," Journal of Neuroscience 27(44): 12007-12011 (Oct. 31, 2007).

Stafstrom et al., "Anticonvulsant and antiepileptic actions of 2-deoxy-D-glucose in epilasy models" Ann Neurol. 65(4) 435-47 Apr. 2009.

Stafstrom et al., "Seizure suppression via glycolysis inhibition with 2-deoxy-D-glucose (2DG) Epilepsia," 49 Suppl. 8:97-100 Nov. 2008.

Velisek et al., "Metabolic environment in substantia nigra reticulata is critical for the expression and control of hypoglycemia-induced seizures," J. Neurosci. 28(38)9349-62 Sep. 17, 2008.

Lian et al., "Frutose-1,6-Bisphosphate has anticonvulsant activity in models of acute seizures in adult rats," J. Neurosci. 27(44)12007-11 Oct. 31, 2007.

Huang et al., "Inhibiting glycolysis to reduce seizures: how it might work," Nat. Neurosci. 9(11)1351-2 Nov. 2006.

Hoesch et al., "Coma after Global Ischemic Brain Injury: Pathophysiology and Emerging Therapies," Critical Care Clinics (24)25-44 Jan. 2008.

DeLorenzo et al., "Comparisons of the mortality and clinical presentations of status epilepticus in private practice community and university hospital settings in Richmond, Virginia," Seizure (18)405-411 (2009).

Bladin et al., "Seizures after Stroke" Arch Neurol (57) 1617-22 Nov. 2000.

\* cited by examiner

COMPOUNDS AND METHODS FOR TREATING SEIZURE DISORDERS

This application claims priority to U.S. Provisional Patent Applications, Ser. No. 60/580,436, filed Jun. 17, 2004, which is explicitly incorporated by reference herein.

This invention was made with government support under grant No. NS025020 by the National Institutes of Health. The government has certain rights in the invention.

BACKGROUND OF THE INVENTION

1. Field of the Invention

This invention relates to methods for alleviating paroxysmal disorders in an animal. The invention particularly relates to relieving epilepsy, by modulating glycolysis in brain cells while maintaining the metabolic integrity thereof. The invention specifically relates to the use of antiglycolytic compounds such as 2-deoxy-D-glucose (2-DG) as anticonvulsant and antiepileptic agents for the treatment of seizures, epilepsy and other paroxysmal alterations in neurological and neuropsychiatric function, including pain and particularly neuropathic pain.

2. Background of the Invention

Functions of the central nervous system may be impaired by a variety of paroxysmal alterations including seizures, syncope, pain, migraine, and transient ischemia. The nerve cells of the brain function in a highly complex but organized manner. A sudden temporary interruption in some or all of the functions of the nerve cells results in a "seizure". Each individual has a "seizure threshold" or level of resistance to seizures: this threshold varies from person to person, most likely due to their genetic makeup and other developmental factors (Stafstrom, 1998, *Pediatrics in Review* 19: 335-344).

A person with a tendency to have repeated seizures may be suffering from epilepsy. Epilepsy is a generic term for a common serious neurological condition that affects one in every 200 adults and one in every 100 children (Hauser & Hersdorffer, 1990, EPILEPSY: FREQUENCY, CAUSES AND CONSEQUENCES, New York: Demos). Epilepsy is defined by recurrent episodes of seizures, which are brief involuntary behavioral alterations caused by paroxysmal intense electrical discharges in the brain. The causes of epilepsy are heterogeneous and include a diverse variety of genetic, metabolic, developmental, traumatic, neoplastic, and vascular etiologies which may present at any time from birth to senescence.

The diagnosis of epilepsy is based on clinical judgment, and may be supported by electroencephalogram, and in some cases, by MRI and blood tests. Seizures can be regarded as symptomatic manifestations of the underlying etiology or pathology. Epilepsy can sometimes be ameliorated by directly treating the underlying etiology, but anticonvulsant drugs, such as phenyloin, gabapentin, lamotrigine, felbamate, and topiramate, and others, which suppress the abnormal electrical discharges and seizures, are the mainstay of conventional treatment (Rho & Sankar, 1999, *Epilepsia* 40: 1471-1483). Currently available anticonvulsant drugs are effective in suppressing seizures in about 50% of patients, are moderately effective and reduce seizures in another 30-35%, and are ineffective in the remaining 15-20% of patients. The mechanisms of action of the currently-used anticonvulsant drugs are complex and for the most part uncertain, but common general modes of anticonvulsant action include antagonism of sodium ion ($Na^+$) channel function (which modifies repetitive use-dependent neuronal discharge), and modifications in γ-aminobutyric acid and glutamate-mediated synaptic transmission (which favorably alter the balance of excitation and inhibition in neural circuits). These drugs are also effective for treatment of other paroxysmal disorders including syncope, convulsive syncope, migraine, neuropathic pain, and neuropsychiatric conditions with paroxysmal or intermittent behavioral disturbances including bipolar disorders, affective disorders, anxiety disorders, stress disorders, and impulse disorders. In addition, anticonvulsants also provide neuroprotection and reduce infarct size in experimental models of stroke and ischemia.

Neurosurgery is an alternative treatment modality in a small proportion of people for whom drug treatment is ineffective. Patients who continue to have recurring seizures despite treatment with contemporary medications (~50% of patients) are regarded as medically intractable, and a subset of these patients demonstrate progressive features such as increasing seizure frequency and cognitive decline. Patients with medically intractable epilepsy are usually considered for surgical resective treatment, which may be curative when a localized irritative lesion can be identified. However, certain patients with intractable epilepsy are not candidates for surgical treatment because of the existence of multiple irritative lesions in these patients. This is especially true for children, for whom there is a subset that do not respond well with antiepileptic medications. For such patients, an alternative therapeutic modality is diet, specifically a high-fat diet known as the "ketogenic diet." In many cases the ketogenic diet may produce effective and sometimes dramatic suppression of seizures and improvements in cognitive function.

The ketogenic diet has been employed for decades in children with epilepsy who have not adequately responded to medical therapy with conventional anticonvulsants (Wilder, 1921, *Mayo Clinic Proceedings* 2: 307-308; Freeman et al., 1998, *Pediatrics* 102: 1358-1363). The anticonvulsant action of the diet, which derives calories from high fat intake with very low or no carbohydrates and only adequate protein for growth, is associated with ketosis and production of the ketones β-hydroxybutyrate and acetoacetate. The ketogenic diet can be significantly efficacious and reduce seizures in a substantial subset of patients with severe epilepsy, but understanding of how the diet produces anticonvulsants effects has been limited. One of the remarkable features of the ketogenic diet is that the anticonvulsant effect develops during a period of at least days to weeks after beginning the diet, but is rapidly lost with intake of even very minimal amounts of carbohydrate. Although the diet induces ketosis and generates ketone bodies (inter alia, β-hydroxybutyrate and acetoacetate), in experimental models ketone bodies are not consistently correlated with the anticonvulsant or anti-epileptic effects (Stafstrom & Bough, 2003, *Nutritional Neuroscience* 6: 67-79; Bough et al., 1999, *Developmental Neuroscience* 21: 400-406).

Despite its general efficacy, treating patients with the ketogenic diet, particularly children, has several drawbacks. Initiation of the diet typically requires hospitalization for up to one week, and the effects and benefits of the diet (i.e., seizure reduction) are usually not experienced immediately, being delayed from one week to three months from when the diet is started. Maintenance of the diet is difficult, since it requires a balance of nutrients at a particular ratio (usually 3:1 to 4:1 fats to all other nutrients) and intake of even a minimal amount of carbohydrates can eliminate the seizure-relieving benefits of the diet. Side-effects of the diet itself include nausea, vomiting, constipation, depression, sleepiness, lethargy, crankiness, decreased alertness, kidney stones, weight gain, increased serum cholesterol, and acidosis (Ballaban-Gil et al., 1998, *Epilepsia* 39: 744-748). In addition, the diet has limited effectiveness in adults, and can be even more difficult to implement with children who are allergic to dairy products.

Thus, there is a need in this art to develop methods and compounds for treating epilepsy, particularly medically-intractable epilepsy using alternatives to currently-available anti-epileptic drugs and neurosurgery. There is also a need to develop therapeutically-effective dietary methods other than the ketogenic diet that are easier to implement and maintain and that have fewer side effects and less severe consequences for non-compliance.

SUMMARY OF THE INVENTION

This invention provides methods for alleviating paroxysmal disorders, particularly epilepsy, convulsions and neuropathic pain, by modulating glycolysis and other metabolic pathways which are altered secondarily to glycolytic modulation in cells involved in initiating, maintaining or perpetuating paroxysmal disorders in the animal. In preferred embodiments, the animal is a human, more preferably a human with epilepsy and most preferably adult or juvenile humans with medically-refractory or drug-resistant epilepsy.

The invention provides methods for treating paroxysmal disorders, particularly epilepsy, convulsions and neuropathic pain in an animal, comprising the step of administering an effective amount of an antiglycolytic compound to an animal in need thereof. In preferred embodiments, the antiglycolytic compound inhibits a glycolytic enzyme, including but not limited to hexokinase (E.C. 2.7.1.1), glucokinase (E.C. 2.7.1.2), glucose-1-phosphate isomerase (E.C. 5.3.1.9), 6-phosphofructo-1-kinase (E.C. 2.7.1.11), fructose bisphosphate aldolase (E.C. 4.1.2.13), glyceraldehyde-3-phosphate dehydrogenase (E.C. 1.2.1.12), triose phosphate isomerase (E.C. 5.3.1.1), phosphoglycerate kinase (E.C. 2.7.2.3), phosphoglyceromutase (E.C. 5.4.2.1), or pyruvate kinase (E.C. 2.7.1.40). In preferred embodiments, the compound is 2-deoxyglucose (2-DG) or derivatives thereof that are converted to 2-deoxyglucose in an animal. In alternative embodiments, the compound is a related deoxy-substitution of glucose, such as 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n). Further embodiments include sugars that can be metabolized into 2-DG, such as 2-deoxy-D-galactose, as well as disaccharide embodiments such as lactose and sucrose analogues containing 2-DG, and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as 3-bromopyruvate. In alternative embodiments, antiglycolytic compounds according to this invention inhibit a glucose transporter, including but not limited to GLUT1 (encoded by the SLC2A1 gene, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT11 (SLC2A11, AP000350), GLUT12 (SLCA12, AL449363), or GLUT13 (SLCA13, AJ315644). In yet additional alternative embodiments, the method further comprises the step of contacting the cells with an amount of lactate, pyruvate, acetoacetate or beta-hydroxybutyrate sufficient to support metabolic integrity in the cells. Preferably, the paroxysmal disorder is epilepsy, most preferably medically-refractory or drug-resistant epilepsy. In a preferred embodiment, seizure frequency or occurrence are reduced by about 50%, more preferably by about 75% and most preferably by about 95%. Alternatively, the paroxysmal disorder is neuropathic pain.

The invention provides methods for preventing paroxysmal disorders, particularly epilepsy, convulsions and neuropathic pain, in an animal, comprising the step of administering an effective amount of an antiglycolytic compound to an animal in need thereof. In preferred embodiments, the antiglycolytic compound inhibits a glycolytic enzyme, including but not limited to hexokinase (E.C. 2.7.1.1), glucokinase (E.C. 2.7.1.2), glucose-1-phosphate isomerase (E.C. 5.3.1.9), 6-phosphofructo-1-kinase (E.C. 2.7.1.11), fructose bisphosphate aldolase (E.C. 4.1.2.13), glyceraldehyde-3-phosphate dehydrogenase (E.C. 1.2.1.12), triose phosphate isomerase (E.C. 5.3.1.1), phosphoglycerate kinase (E.C. 2.7.2.3), phosphoglyceromutase (E.C. 5.4.2.1), or pyruvate kinase (E.C. 2.7.1.40). In preferred embodiments, the compound is 2-deoxyglucose or a derivative of 2-DG that is converted to 2-DG in an animal. In alternative embodiments, the compound is a related deoxy-substitution of glucose, such as 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n). Further embodiments include sugars that can be metabolized into 2-DG, such as 2-deoxy-D-galactose, as well as disaccharide embodiments such as lactose and sucrose analogues containing 2-DG, and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as 3-bromopyruvate. In alternative embodiments, antiglycolytic compounds according to this invention inhibit a glucose transporter, including but not limited to GLUT1 (encoded by the SLC2A1 gene, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT11 (SLC2A11, AP000350), GLUT12 (SLCA12, AL449363), or GLUT13 (SLCA13, AJ315644). In yet additional alternative embodiments, the method further comprises the step of contacting the cells with an amount of lactate, pyruvate, acetoacetate or beta-hydroxybutyrate sufficient to support metabolic integrity in the cells. Preferably, the paroxysmal disorder is epilepsy, most preferably medically-refractory or drug-resistant epilepsy. In a preferred embodiment, seizure frequency or occurrence are reduced by about 50%, more preferably by about 75% and most preferably by about 95%. Alternatively, the paroxysmal disorder is neuropathic pain.

In certain additional embodiments, the methods provided by the invention reduce epileptic synchronous bursting in neural cells and in brain slices. In these embodiments, the methods comprise the step of contacting the cells with an effective amount of an antiglycolytic compound. In preferred embodiments, the antiglycolytic compound inhibits a glycolytic enzyme, including but not limited to hexokinase (2.7.1.1), glucokinase (2.7.1.2), glucose-1-phosphate isomerase (5.3.1.9), 6-phosphofructo-1-kinase (2.7.1.11), fructose bisphosphate aldolase (4.1.2.13), glyceraldehyde-3- phosphate dehydrogenase (1.2.1.12), triose phosphate isomerase (5.3.1.1), phosphoglycerate kinase (2.7.2.3), phosphoglyceromutase (5.4.2.1), or pyruvate kinase (2.7.1.40). In preferred embodiments, the compound is 2-deoxyglucose or a derivative of 2-DG that is converted to 2-DG in an animal. In alternative embodiments, the compound is a related deoxy-substitution of glucose, such as 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n). Further embodiments include sugars that can be metabolized into 2-DG, such as 2-deoxy-D-galactose, as well as disaccharide embodiments such as lactose and sucrose analogues containing 2-DG, and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as 3-bromopyruvate. In alternative embodiments, the antiglycolytic compound inhibits a glucose transporter, including but not limited to GLUT1 (SLC2A1, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT11 (SLC2A11, AP000350), GLUT11 (SLC2A11, AP000350), GLUT12 (SLCA12, AL449363), or GLUT13 (SLCA13, AJ315644). Preferably, the neural cells are mammalian, more preferably human, and most preferably adult or juvenile human neural cells.

In additional embodiments, the methods provided by the invention prevent or are used to treat pain, particularly neuropathic pain, in an animal. In these embodiments, the methods comprise the step of administering to the animal an effective amount of an antiglycolytic compound. In preferred embodiments, the antiglycolytic compound inhibits a glycolytic enzyme, including but not limited to hexokinase (2.7.1.1), glucokinase (2.7.1.2), glucose-1-phosphate isomerase (5.3.1.9), 6-phosphofructo-1-kinase (2.7.1.11), fructose bisphosphate aldolase (4.1.2.13), glyceraldehyde-3-phosphate dehydrogenase (1.2.1.12), triose phosphate isomerase (5.3.1.1), phosphoglycerate kinase (2.7.2.3), phosphoglyceromutase (5.4.2.1), or pyruvate kinase (2.7.1.40). In preferred embodiments, the compound is 2-deoxyglucose or a derivative of 2-DG that is converted to 2-DG in an animal. In alternative embodiments, the compound is a related deoxy-substitution of glucose, such as 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n). Further embodiments include sugars that can be metabolized into 2-DG, such as 2-deoxy-D-galactose, as well as disaccharide embodiments such as lactose and sucrose analogues containing 2-DG, and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as 3-bromopyruvate. In alternative embodiments, the antiglycolytic compound inhibits a glucose transporter, including but not limited to GLUT1 (SLC2A1, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT11 (SLC2A11, AP000350), GLUT11 (SLC2A11, AP000350), GLUT12 (SLCA12, AL449363), or GLUT13 (SLCA13, AJ315644). Preferably, the animal is a mammal, more preferably a human and particularly a human suffering from neuropathic pain.

The invention also provides pharmaceutical compositions comprising 2-deoxyglucose or derivatives thereof that are converted to 2-DG in an animal, or related deoxy-substituted glucose compounds, such as 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n), sugars that can be metabolized into 2-DG, such as 2-deoxy-D-galactose, as well as disaccharide embodiments such as lactose and sucrose analogues containing 2-DG, and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as 3-bromopyruvate, formulated to be used according to the methods of the invention. The pharmaceutical compositions of the invention are provided formulated with pharmaceutically-acceptable excipients, adjuvants, or other components adapted to the mode of administration, including but not limited to oral, parenteral and topical administration routes.

The methods of the invention are advantageous because they involve administration of compounds that are less toxic or that have fewer or more mild side-effects than the anticonvulsant and anti-epileptic drugs currently used to treat seizure disorders. The methods of the invention are also advantageous over dietary methods, such as the ketogenic diet known in the prior art, due to ease of implementation, easier and more likely compliance with their administration, less opportunity to avoid or neglect treatment compliance, smaller effects on serum lipids and cholesterol levels, less weight gain, more immediate effectiveness, and ease of monitoring. The inventive methods are advantageous as compared to neurosurgery in being less invasiveness and less irreversible.

Specific preferred embodiments of the present invention will become evident from the following more detailed description of certain preferred embodiments and the claims.

DESCRIPTION OF THE DRAWINGS

An understanding of the invention is facilitated by reference to the drawings.

FIG. 2A illustrates the effects of 2-DG on the AD threshold of rats that experienced kindled seizures evoked by stimulation of the perforant path with 1 sec trains of 62 hertz 1 msec. FIG. 2B demonstrates that 2-DG impairs the progression of kindling evoked by stimulation of the perforant path. In rats treated with 2-DG in a dose of 250 mg/kg intraperitoneally (IP) at 30 minutes before stimulation, more seizures were required to reach milestones of Class III, IV, and V seizures. This demonstrates that 2-DG in not only anticonvulsant by increasing the AD (seizure) threshold, but also has antiepileptic effects by slowing the progression of kindling in response to repeated seizures.

FIG. 4A demonstrates a multispike extracellular field recording of spontaneous epileptic discharges shown at slower speeds in FIGS. 4B and 4C. The baseline frequency of epileptic discharges is illustrated in FIG. 4B, and FIG. 4C is the frequency after bath application of 1 mM 2-DG. These recordings demonstrated reduction in epileptic bursts by bath application of 2-DG.

DETAILED DESCRIPTION OF THE PREFERRED EMBODIMENTS

Figure 1:
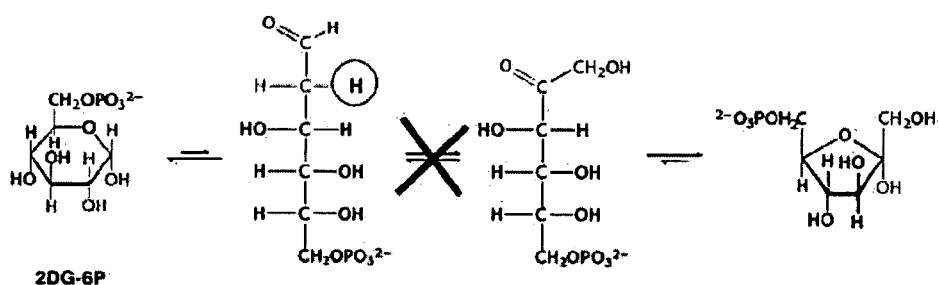
FIG. 1 is a schematic diagram of a portion of the chemical reactions and enzymatic mediators thereof occurring in glycolysis in a mammalian cell, showing inhibition of glucose-6-phosphate dehydrogenase by 2-DG.

The invention provides methods and compounds for alleviating paroxysmal disorders, particularly epilepsy, convulsions and neuropathic pain, in an animal, particularly humans and including children having medically intractable epilepsy. The methods provided by the invention relate to reducing seizures in an animal by modulating glycolysis in brain cells thereof involved in provoking, initiating or maintaining the seizure disorder. The methods of the invention specifically involve administering a therapeutically effective amount of an antiglycolytic compound to the animal, particularly 2-deoxyglucose or related compounds, as set forth herein, in an amount effective in having an antiglycolytic effect in brains of epileptic animals.

As used herein, the term "antiglycolytic compound" is intended to encompass compounds that modulate glucose metabolism, particularly in brain cells involved in epileptic or synchronized bursting or in the brains of animals suffering from paroxysmal disorders, particularly epilepsy, convulsions and neuropathic pain, preferably humans and most preferably adult or juvenile humans with epilepsy. The term specifically encompasses compounds that inhibit glycolytic enzymes, particularly hexokinase (E.C. 2.7.1.1), glucokinase (E.C. 2.7.1.2), glucose-1-phosphate isomerase (E.C. 5.3.1.9), 6-phosphofructo-1-kinase (E.C. 2.7.1.11), fructose bisphosphate aldolase (E.C. 4.1.2.13), glyceraldehyde-3-phosphate dehydrogenase (E.C. 1.2.1.12), triose phosphate isomerase (E.C. 5.3.1.1), phosphoglycerate kinase (E.C. 2.7.2.3), phosphoglyceromutase (E.C. 5.4.2.1), or pyruvate kinase (E.C. 2.7.1.40). The term also includes compounds that inhibit glucose transporter proteins, particularly glucose transporters known in the art as GLUT1 (SLC2A1, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT11 (SLC2A11, AP000350), GLUT11 (SLC2A11, AP000350), GLUT12 (SLCA12, AL449363), or GLUT13 (SLCA13, AJ315644). In preferred embodiments, an antiglycolytic compound of the invention is 2-deoxyglucose or derivatives thereof that are converted to 2-DG in an animal, or a related deoxy-substitution of glucose, such as 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n). In additional preferred embodiments, the antiglycolytic compound is a sugar that can be metabolized into 2-DG, such as 2-deoxy-D-galactose, as well as disaccharide embodiments such as lactose and sucrose analogues containing 2-DG, and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as 3-bromopyruvate. More preferably, an antiglycolytic compound of the invention is 2-deoxy-D-glucose (2-DG) or 3-bromopyruvate, which also inhibit enzymes of the glycolytic pathway.

As used herein, the term "paroxysmal disorder" includes but is not limited to seizure disorders such as infantile spasms, myoclonic and "minor motor" seizures, as well as tonic-clonic seizures and partial complex seizures. In preferred embodiments, the seizure disorder is epilepsy, including idiopathic, symptomatic and cryptogenic epilepsy, and more preferably drug-resistant or medically-refractory epilepsy, by which is meant that epileptic seizures continue despite adequate administration of antiepileptic drugs.

As used herein, the term "paroxysmal disorders" also includes syncope, convulsive syncope, migraine, pain, tics, tremors and other movement disorders, and neuropsychiatric conditions with paroxysmal or intermittent behavioral disturbances including bipolar disorders, affective disorders, anxiety disorders, and stress disorders.

In particular, chronic pain and neuropathic pain are regarded as a paroxysmal disorder as the symptoms not only spontaneously vary in intensity and severity, but arise from electrical impulse generation originating in damaged or injured nerves or in response to tissue injury. Neuropathic pain is a common clinical disorder associated with injury and dysfunction involving the peripheral and central nervous system. The characteristic features of neuropathic pain include paresthesias, allodynia (painful responses to normally innocuous tactile stimuli), and hyperalgesia (increased responses to noxious stimuli). Neuropathic pain is a condition which develops and often progresses in association with a variety of initial injuries and diverse etiologies such as direct neural trauma, infections, amputations, surgery, diabetes, and other metabolic disturbances. It is increasingly appreciated that many of the chronic features of neuropathic pain may be a result of molecular, cellular, and circuit level processes in the peripheral and central nervous systems that are consequences not only of the initial injury, but also ongoing neural activity and ectopic impulse generation. For these reasons, the pathogenesis of neuropathic pain can be viewed as a phenomenon of activity-dependent neural plasticity. Those skilled in the art have attempted to treat neuropathic pain with analgesics, but these agents generally provide symptomatic relief in only a subset of patients only for the duration of therapy and some anticonvulsants such as gabapentin (GBP) may be partially effective in this disorder. Consequently, neuropathic pain is at best only partially and temporarily relieved in a minority of patients and more effective treatment is clearly needed.

As used herein, the term "juvenile," particularly when applied to a human patient is a human less than 18 years old, more preferably less than 16 years old, more preferably less than 14 years old, more preferably less than 12 years old, most preferably less than 10 years old.

As used herein, the term "ketogenic diet" is intended to describe low carbohydrate, high fat diets used as an alternative to drug therapy for epilepsy in children. In the "classic" form of the diet, calories are provided from food naturally high in fats, such as cream, cheese, mayonnaise, butter and oil. In this form, the proportion of fats to carbohydrates and protein in the diet is about 4:1 (by weight, equivalent to a 9:1 ratio by caloric content). In an alternative form, the diet is supplemented with medium chain triglycerides (MCT). The ketogenic diet has been employed for decades in children with epilepsy who have not adequately responded to medical therapy with conventional anticonvulsants. The anticonvulsant action of the diet, which derives calories from high fat and protein intake with very low or no carbohydrates, is associated with ketosis and production of the ketones β-hydroxybutyrate and acetoacetate. The "ketogenic" diet can be significantly efficacious and reduce seizures in a substantial subset of patients with severe epilepsy, but understanding of how the diet produces anticonvulsant effects is limited. One of the remarkable features of the ketogenic diet is that the anticonvulsant effect is rapidly lost with intake of very minimal amounts of carbohydrate. Most research has focused on the role of ketone bodies for the anti-epileptic effect of the diet, but have not addressed the observed peculiarity that the anticonvulsant effects of the diet are rapidly lost with minimal carbohydrate intake.

As used herein, "antiepileptic drugs" include but are not limited to gabapentin (Neurontin), carbamazepine (Tegretol), ethosuximide (Zarontin), lamotrigine (Lamictal), felbamate (Felbatol), topiramate (Topamax), zonisamide (Zonergran), tiagabine (Gabitril), oxcarbazepine (Trileptal), levetiracetam (Keppra), divalproex sodium (Depakote), phenyloin (Dilantin), fos-phyenytoin (Cerebryx).

As used herein, an "effective amount" or "therapeutically effective amount" of an antiglycolytic compound is defined as an amount that when administered to an animal, preferably a human, more preferably a human having a paroxysmal disorder including both adults and juvenile humans with epilepsy, reduces the frequency, duration or severity of seizures experienced by the individual. The "effective amounts" of said antiglycolytic compounds are those doses that produce subnanomolar to millimolar concentrations of a compound such as 2-deoxyglucose in blood or plasma, and will depend on species, pharmacokinetics, and route of administration. In rats, an "effective dose" of 2-DG is 250 mg/kg by intraperitoneal or subcutaneous administration, but lesser doses may also be effective.

As used herein the term "metabolic integrity" is intended to mean that the cell is viable and metabolically active, and specifically is not apoptotic or metabolically impaired by existence in a low glucose environment. The term in particular is intended to mean that the energy balance of the cell and its capacity to meet its normal energetic requirements is maintained.

Glycolysis is the metabolic pathway for obtaining energy from glucose, and is illustrated in FIG. 1. The utilization of glucose as an energy source requires entry into the cell by specific hexose transporters, including but not limited to GLUT1 (SLC2A1, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT11 (SLC2A11, AP000350), GLUT11 (SLC2A11, AP000350), GLUT12 (SLCA12, AL449363), or GLUT13 (SLCA13, AJ315644). After entry into the cell, glucose is phosphorylated to form 6-phospho-glucose (6-P-G); this phosphorylation is performed by hexokinases, which are expressed ubiquitously in mammalian tissues, and glucokinases, which are expressed in liver and in some brain cells. 6-P-G is then isomerized to form 6-phospho-fructose by phosphoglucose isomerase (E.C. 5.3.1.9). This reaction requires the opening of the 5-carbon glucose ring followed by closure to form a 4-carbon ring, which occurs by oxidation of the 2-carbon hydroxyl group to a keto group. 6-phospho-fructose is in turn phosphorylated to 1,6 diphosphofructose by 6-phosphofructose-1-kinase (E.C. 2.7.1.11), and this compound is cleaved to glyceraldehyde-3-phosphate and dihydroxyacetone phosphate by fructose bisphosphate aldolase (E.C. 4.1.2.13). The dihydroxyacetone phosphate formed in this reaction is converted to glyceraldehyde-3-phosphate, which is the substrate for glyceraldehyde-3-phosphate dehydrogenase (E.C. 1.2.1.12), forming 1,3 phosphoglycerate. 1,3 phosphoglycerate is converted to 3-phosphoglycerate by 3-phosphoglycerate kinase (E.C. 2.7.2.3), and the 3-phosphoglycerate product of this reaction is converted to 2-phosphoglycerate by phosphoglyceromutase (E.C. 5.4.2.1). The enzyme enolase (E.C. 4.2.1.11) converts 2-phosphoglycerate to phosphoenol pyruvate, which then forms pyruvate by the action of pyruvate kinase (E.C. 2.7.1.40). Pyruvate can then be converted to lactate or acetyl-CoA, depending on metabolic conditions in the cell.

Certain of the antiglycolytic compounds provided by the invention, and methods for using them as anticonvulsants and anti-epileptic agents, inhibit at least one of the enzymes that mediate glycolysis. In preferred embodiments, 2-DG inhibits conversion of 6-phosphoglucose to fructose-6-phosphate due to the lack of an hydroxyl group at the 2-carbon position, resulting in a shutdown of the glycolytic pathway. Thus, 2-DG acts as a "low calorie mimic" because it prevents utilization of glucose otherwise present in the diet and available for metabolic breakdown. In alternative embodiments, other glycolysis inhibitors can be used that inhibit, for example, glyceraldehyde-3-phosphate dehydrogenase (E.C. 1.2.1.12), such as 3-bromopyruvate, and halogenated analogues of glycolytic intermediates, such as 1,6-dichloro-1,6-dideoxy-D- fructofuranose (dichlorodideoxyfructose, DCF), 1-chloro-3-hydroxypropanone, and bromopyruvate. Other preferred embodiments are halogenated derivatives of 2-DG such as 2-fluoro-deoxyglucose-D-glucose In alternative embodiments, other deoxy derivatives of hexose sugars that are useful in the practice of the methods of the invention include 2-deoxy galactose. These compounds function in a analogous manner and prevent galactose from being used as a carbon source. Alternative embodiments also include 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n), sugars that can be metabolized into 2-DG, such as 2-deoxy-D-galactose, as well as disaccharide embodiments such as lactose and sucrose analogues containing 2-DG, and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as 3-bromopyruvate, formulated to be used according to the methods of the invention.

In certain embodiments, the present invention specifically the provides antiglycolytic compounds 2-deoxy-D-glucose (2-DG) and pharmaceutical formulations thereof as an anticonvulsant and antiepileptic agent for the treatment of seizures, epilepsy and other paroxysmal alterations in neurological and neuropsychiatric dysfunction. This invention includes antiglycolytic compounds that are 2-DG and related deoxy-substitutions of glucose (as described above), halogenated derivatives and conjugates of these compounds that also block glycolysis, sugars such as 2-deoxy-D-galactose and other compounds that are metabolized into 2-DG and act in the central nervous system by inhibiting glycolysis, and compounds modifying reactions in other metabolic pathways that mimic the effects of glycolytic inhibition on those pathways and have anticonvulsant and antiepileptic effects.

As disclosed herein, 2-DG had anticonvulsant and antiepileptogenic effects against seizures evoked in vivo in rats by kindling stimulation, a well-characterized and art-accepted model of seizures and epilepsy induction. 2-DG was also effective against epileptic discharges evoked in vitro by elevation of extracellular K concentration $[K^+]_o$. 2-DG acts in the central nervous system by inhibiting glycolysis, which also has associated effects on other metabolic pathways that may cumulatively influence energy generation, intracellular signaling pathways, and long-term regulation of cellular function, making it a useful treatment for paroxysmal alterations in neurological and neuropsychiatric function such as seizures, epilepsy, migraine, syncope, pain, anxiety, and mood disorders.

2-DG is known in the art and itself and derivatives thereof have been used medicinally, particularly as a radiolabeled tracer molecule in positron emission tomography (PET) scans of myocardium for diagnosing ischemic heart disease and brain seizures in humans, as well as certain malignancies (see www.fda.gov/cder/regulatory/pet/fdgoncologyfinal.htm, visited Dec. 23, 2003). 2-DG has also been used as a chemotherapeutic agent against breast cancer (Kaplan et al., 1990, Cancer Research 50: 544-551).

As provided herein, pharmaceutical compositions comprising 2-DG and methods using said compositions will be understood to encompass preparations of 2-deoxyglucose as the D-stereoisomer, as well as racemic mixtures thereof comprising any combination of D- and L-2-deoxyglucose, provided that the percentage of the D-stereoisomer is greater than zero. 2-DG is available commercially, and preferably is produced according to the standards and guidelines of the pharmaceutical industry and in compliance with all relevant regulatory requirements. 2-DG can also be synthesized using methods well-established in the art (see, for example, THE MERCK INDEX, $12^{th}$ Ed., Monograph 2951, New Jersey: Merck & Co., 1997; Bergmann et al., 1922, Ber. 55: 158; Snowden et al., 1947, JACS 69: 1048; Bolliger et al., 1954, Helv. Chim. Acta 34: 989; Bolliger, 1962, "2-Deoxy-D-arabino-hexose (2-Deoxy-d-glucose)," in METHODS IN CARBOHYDRATE CHEMISTRY, vol. I, (Whistler & Wolfram, eds.), New York Academic Press, pp. 186,189).

The invention also provides embodiments of said antiglycolytic compounds as pharmaceutical compositions. The pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions of the antiglycolytic compounds of the present invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the antiglycolytic compounds in a local rather than systemic manner, for example, via injection of the compound directly into a specific tissue, often in a depot or sustained release formulation. Specifically, antiglycolytic compounds and formulations of the invention can be administered locally by devices and local infusion systems to achieve local effects in tissues.

Pharmaceutical compositions for use in accordance with the methods of the present invention thus can be formulated in conventional manner using one or more physiologically acceptable carriers comprising excipients and auxiliaries that facilitate processing of antiglycolytic compounds into preparations that can be used pharmaceutically. Proper formulation is dependent upon the route of administration chosen.

The antiglycolytic compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the antiglycolytic compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use. The compounds can also be formulated in rectal compositions such as suppositories or retention enemas, e.g. containing conventional suppository bases such as cocoa butter or other glycerides.

For injection, antiglycolytic compounds can be formulated in appropriate aqueous solutions, such as physiologically compatible buffers such as Hank's solution, Ringer's solution, lactated Ringer's solution, or physiological saline buffer. For transmucosal and transcutaneous administration, penetrants appropriate to the barrier to be permeated are used in the formulation. Such penetrants are generally known in the art.

For oral administration, antiglycolytic compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose and starch preparations such as, for example, maize starch, wheat starch, rice starch, potato starch, gelatin, gum tragacanth, microcrystalline cellulose, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, antiglycolytic compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation antiglycolytic compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

In addition to the formulations described previously antiglycolytic compounds can also be formulated as a depot preparation. Such long acting formulations can be administered by implantation (for example subcutaneously or intramuscularly) or by intramuscular injection. Thus, for example, the antiglycolytic compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for hydrophobic embodiments of the antiglycolytic compounds of the invention is a co-solvent system comprising benzyl alcohol, a nonpolar surfactant, a water-miscible organic polymer, and an aqueous phase. The co-solvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems can be employed. Liposomes and emulsions are well known examples of delivery vehicles or carriers for hydrophobic drugs. Certain organic solvents such as dimethylsulfoxide also can be employed, although usually at the cost of greater toxicity. Additionally, antiglycolytic compounds can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the antiglycolytic compounds for a few weeks up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

The invention also provides formulations of the antiglycolytic compounds as foodstuffs, food supplements or as a component of a food for an animal, preferably a human, more preferably a human with epilepsy and most preferably adult or juvenile humans with medically-refractory or drug-resistant epilepsy.

For any antiglycolytic compounds used in the method of the invention, the therapeutically effective dose can be estimated initially from in vitro assays, as disclosed herein, or using art-recognized animal model systems or a combination thereof. For example, a dose can be formulated in animal models to achieve a circulating concentration range that includes the $EC_{50}$ (effective dose for 50% increase) as determined in vitro, i.e., the concentration of the test compound which achieves a half-maximal amount of seizure frequency. Such information can be used to more accurately determine useful doses in humans.

It will be understood, however, that the specific dose level for any particular patient will depend upon a variety of factors including the activity of the antiglycolytic compounds employed, body weight, general health, sex, diet, time of administration, route of administration, and rate of excretion, drug combination, the severity and extent of the particular seizure disorder in the patient undergoing therapy and the judgment of the prescribing physician and in particular the age of the patient, who is may be an adult, a juvenile, a child or an infant.

Preferred antiglycolytic compounds provided by the invention will have certain pharmacological properties. Such properties include, but are not limited to oral bioavailability, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcová et al. (1996, *J. Chromat. B* 677: 1-27). In vitro half-lives of antiglycolytic compounds may be predicted from assays of microsomal half-life as described by Kuhnz and Gieschen (1998, *Drug Metabolism and Disposition*, 26: 1120-1127).

Toxicity and therapeutic efficacy of said antiglycolytic compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio between $LD_{50}$ and $ED_{50}$. Antiglycolytic compounds that exhibit high therapeutic indices are preferred. The data obtained from these cell culture assays and animal studies can be used in formulating a range of dosage for use in humans. The dosage of such antiglycolytic compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch.1, p. 1).

For example, dosage amount and interval of 2-DG administration can be adjusted individually to reduce seizure frequency, duration or intensity from doses of 250 mg/kg or less to higher as tolerated to reduce seizure frequency and minimize toxicity. Doses of 650 mg/kg were well tolerated in rats. The anticonvulsant effects of 2-DG administered at 250 mg/kg twice daily for 3 months lasted for approximately 8 weeks after stopping 2-DG while continuing twice daily stimulation, indicating that effects of 2-DG are quite prolonged. A practitioner skilled in the art can adjust dosage in the range up to 500-600 mg/kg and the timing of administration to produce prolonged anticonvulsant and antiepileptic effects. Efficacious dosage amounts can be adjusted to about 14 mg/kg 2-DG in children and 40 mg/kg 2-DG in adults, using therapeutic efficacy measurements (e.g., reduction in frequency or severity of seizures) as a criterion for establishing effective dosage levels.

For the alternative embodiments such as antiglycolytic compounds that reversibly inhibit glycolysis, dosage amount and timing of administration of said compounds can be adjusted individually to provide plasma levels of the antiglycolytic compounds that are sufficient to reduce seizure frequency, duration or intensity.

The pharmaceutical compositions disclosed herein can be administered before, during or after the occurrence of a paroxysmal event such as a seizure, particularly an epileptic seizure, and the route of administration and administered dose chosen accordingly. For example, administration of the pharmaceutical compositions of the invention during a seizure will preferably be in a rapidly-bioavailable dosage using a safe and effective administration route (inter alia, which may not include oral formulations in these embodiments).

The invention provides methods for reducing seizure frequency, duration or intensity in an animal, preferably an adult or juvenile human. The methods of the invention are effective for reducing seizure frequency, duration or intensity in at least 50%, more preferably 60%, more preferably 70%, more preferably 80%, more preferably 90%, more preferably 95%, more preferably 98%, and more preferably 99% of treated patients. In preferred embodiments, the inventive methods are practiced using the pharmaceutical compositions of the invention as disclosed herein.

The Examples which follow are illustrative of specific embodiments of the invention, and various uses thereof. They are set forth for explanatory purposes only, and are not to be taken as limiting the invention.

EXAMPLE 1

Anticonvulsant and Antiepileptic Actions of 2-DG Against Kindled Seizures

Anticonvulsant and antiepileptic effects of 2-deoxyglucose (2-DG) were evaluated in the kindling model of temporal lobe epilepsy.

In the kindling model, repeated activation of neural pathways in vivo induces progressive electrographic and behavioral seizures, permanent increases in susceptibility to additional seizures, and eventually spontaneous seizures (Goddard et al., 1969, *Experimental Neurology* 25: 295-330; Pinel, 1978, *Experimental Neurology* 58: 190-202; Wada et al., 1975, *Canadian Journal of Neurological Sciences* 2: 477-492; Sayin et al. 2003, *Journal of Neuroscience* 23: 2759-2768). Kindling has become the most extensively studied experimental model of epilepsy (McNamara, 1999, *Nature* 399: A15-22). In a typical kindling protocol, periodic stimulation delivered once or twice daily gradually evokes an increasing synchronous electrical afterdischarge (AD) or electrographic seizure accompanied by a behavioral seizure. Once kindled seizures have been repeatedly induced, the susceptibility to repeated seizures is life-long and can thus be regarded as permanent. Kindling can be induced by electrical or chemical activation of a variety of neural pathways in a range of species that include amphibians, mammals, and primates (Morrell and Tsuru, 1976, *Electroencephalography and Clinical Neurophysiology* 40: 1-11); Wada and Mizoguchi, 1984; *Epilepsia* 25: 278-287). Because kindling induces permanent alterations in the brain and can be evoked in a range of species by a variety of stimuli, it has been regarded as a phenomenon of long-term brain plasticity as well as a model of temporal lobe epilepsy. The behavioral features of brief repeated kindled seizures evoked by limbic stimulation resemble human partial complex seizures with secondary generalization. In the early stages of limbic kindling in rodents, each stimulation evokes an AD accompanied by a brief partial seizure, which progresses to stimulus-evoked secondary generalized seizures. This feature is an example of the progressive functional alterations induced by kindling that are epileptogenic.

In vivo experiments to demonstrate the anticonvulsant and antiepileptic effects of 2-DG were performed as follows. Adult male Sprague-Dawley rats (weighing between 250-350 g, obtained from Harlan, Madison, Wis.) were anesthetized with ketamine (80 mg/kg intramuscularly) and xylazine (10 mg/kg intramuscularly), and were stereotactically implanted with an insulated stainless steel bipolar electrode for stimulation and recording. The electrode was implanted in the perforant path (8.1 mm posterior, 4.4 mm lateral, 3.5 mm ventral with respect to bregma), and was fixed to the skull with acrylic. After a two-week recovery period following electrode placement, unrestrained, awake, implanted rats received twice-daily kindling stimulation (5 days per week) with a one-second train of 62-Hertz (Hz) biphasic constant current 1.0-millisecond (ms) square wave pulses to induce kindled seizures. The electroencephalogram was recorded from the bipolar electrode, which was switched to the stimulator for the delivery of kindling stimulation. On the first day of stimulation, each rat received a stimulus train of 500 micro-Amperes ($\mu A$). If an AD was evoked, this intensity was used in subsequent stimulations. If no AD was evoked, the stimulation intensity was increased in a sequence of 500, 700, 900, 1000, 1100, 1200, 1300 and 1400 $\mu A$ until an AD was evoked. The intensity that initially evoked AD was used for subsequent stimulations. If 1400 $\mu A$ failed to evoke AD, stimulation was continued on subsequent days increased through this same intensity sequence until a maximum of 1500 $\mu A$. If AD was evoked by 3 consecutive stimulations at a given intensity, the stimulation intensity was then decreased by 100 $\mu A$ decrements. At stimulation intensities below 500 $\mu A$, the intensity was decreased in 30 $\mu A$ decrements. These stimulation procedures deliver stimulation at the lowest intensity required to evoke an AD (Sutula and Steward, 1986, *Journal of Neurophysiology* 56: 732-746; Cavazos et al., 1991, *Journal of Neuroscience* 11: 2795-2803). Evoked behavioral seizures were classified according to standard criteria and ranged from Class I (behavioral arrest) to Class V seizures (bilateral tonic-clonic motor activity with loss of postural tone), which are comparable to partial complex seizures with secondary generalization.

Figure 2A:
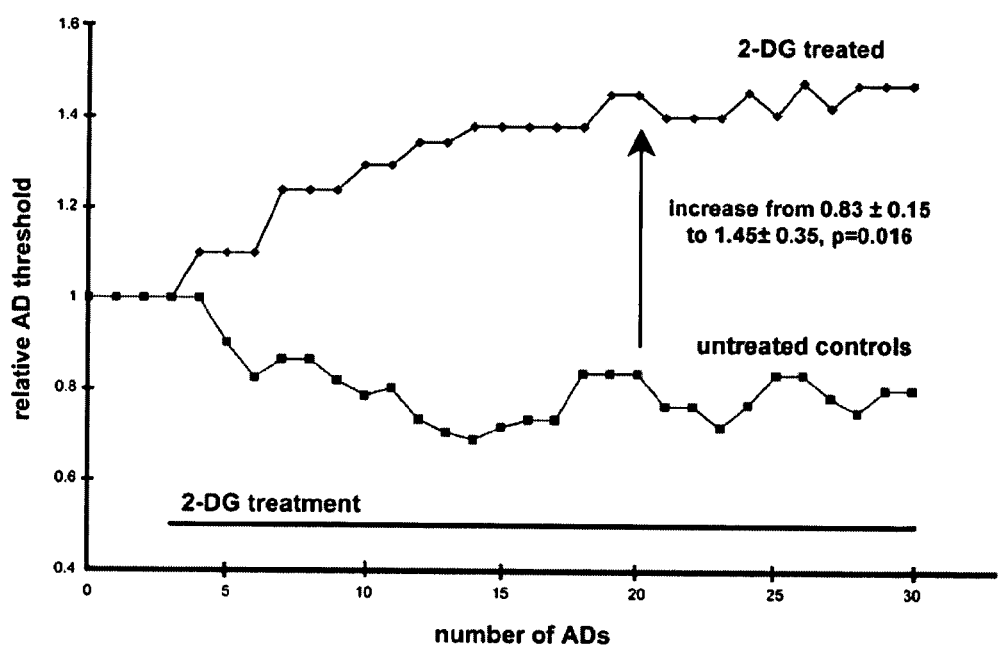
FIGS. 2A and 2B illustrate the effects of 2-DG on the afterdischarge (AD) threshold and demonstrate anticonvulsant and antiepileptic effects of 2-DG against kindled seizures.
Figure 2A:
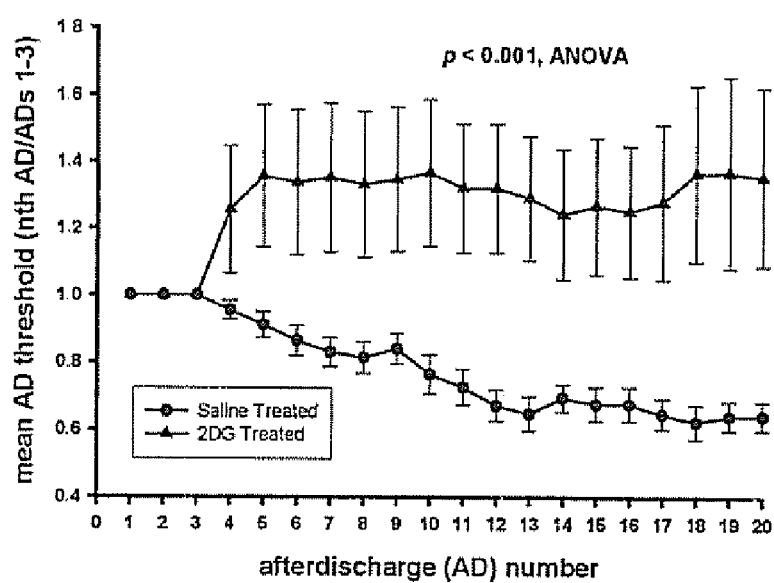
Figure 2B:
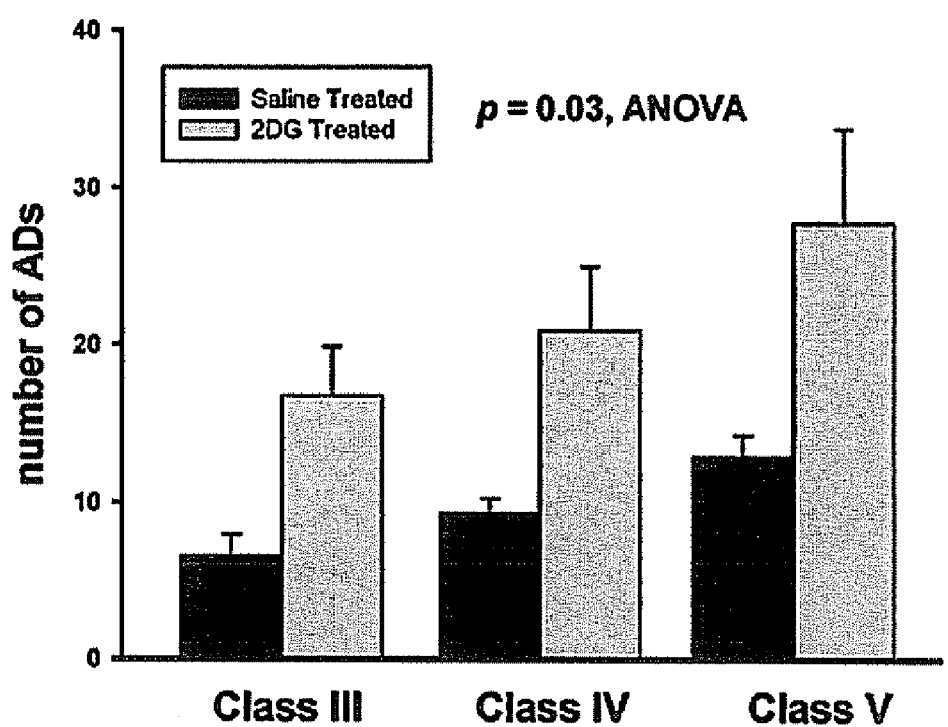
Figure 2C:
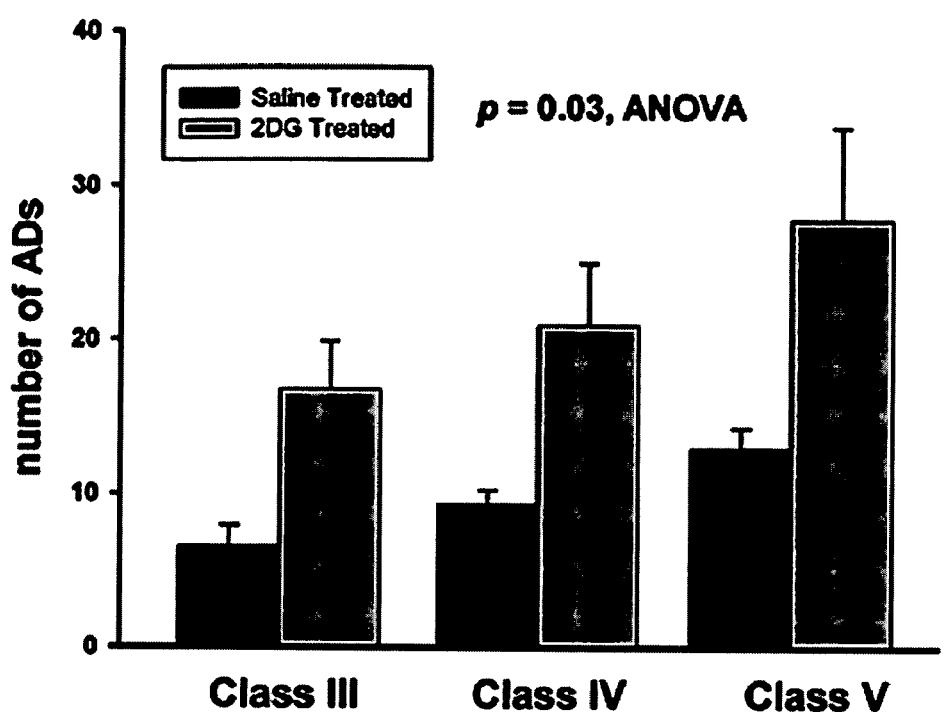

The anticonvulsant and antiepileptic effects of 2-DG were confirmed in rats that experienced kindled seizures evoked by perforant path stimulation according to the protocol noted above. 2-DG increased the AD threshold in rats that received perforant path stimulation (n=15) compared to control rats that received saline (n=12) (p<0.001, ANOVA, FIG. 2A). Rats treated with 2-DG (n=11) that received perforant path stimulation required 27.7±6.0 ADs to reach the milestone of the first Class V generalized tonic clonic seizure compared to 12.9±1.3 ADs in saline treated controls (n=10, p<0.03, t-test). Rats treated with 2-DG required more ADs to reach Class 3, Class 4, and Class 5 seizures than saline treated controls (see Table 1, p<0.03, ANOVA and FIG. 2B).

TABLE 1

|  | ADs to Class 3 | ADs to Class 4 | ADs to Class 5 |
|---|---|---|---|
| 2-DG | 16.7 +/− 3.1 | 20.9 +/− 4.0 | 27.7 +/− 6.0 |
| saline | 6.6 +/− 1.3 | 9.3 +/− 0.9 | 12.9 +/− 1.3 |

Figure 3:
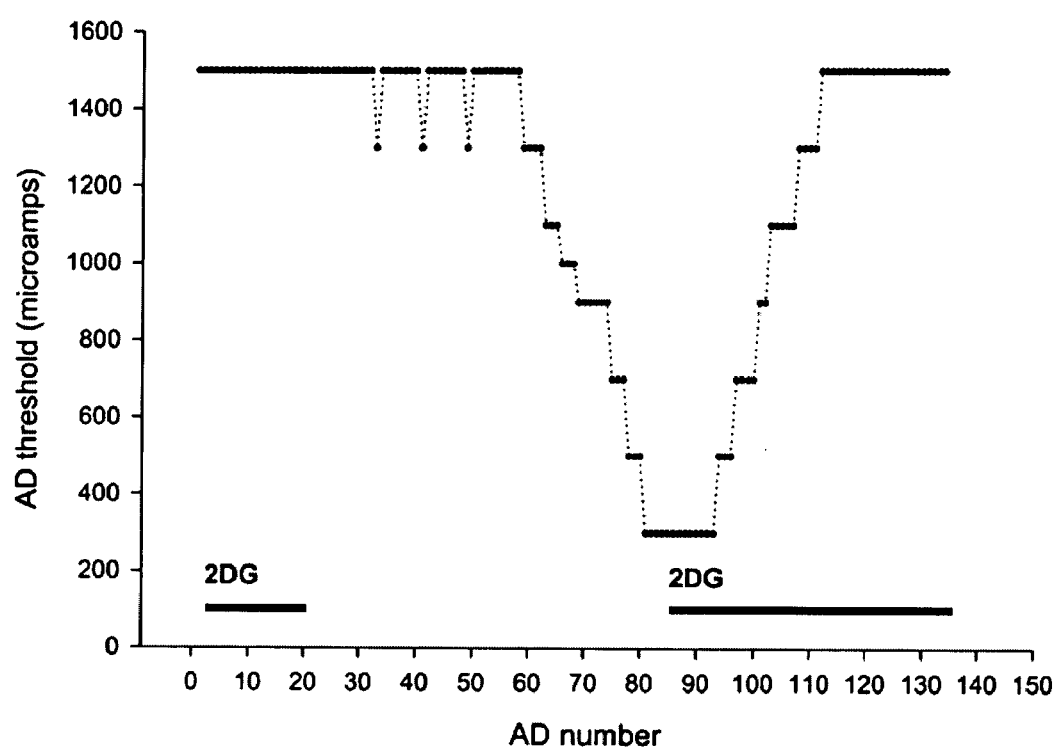
FIG. 3 demonstrates the AD threshold of a rat that was initially experiencing repetitive ADs at an intensity of 1500 μAmps. After the third evoked AD, 2-DG was administered at a dose of 250 mg/kg intraperitoneally (IP) prior to each stimulation (indicated by the first bar just above the x-axis), and appeared to prevent the progressive reduction in AD threshold that is typically observed with repeated ADs evoked by kindling, which is regarded as a measure of progression. The 2-DG treatment was stopped after 20 ADs, after a period of about 8 weeks and ~40 additional ADs, there was a gradual reduction in AD threshold to ~200 μAmps. Administration of 2-DG was then restarted (indicated by the second bar just above the x-axis), and increased the AD threshold to 1500 μAmps during a period of 2-3 weeks.

The effect of 2-DG on the AD threshold is also illustrated in FIG. 3 for a kindled rat experiencing repeated evoked seizures. Repeated evoked seizures were accompanied by a gradual reduction of the AD threshold, which was initially 1500 $\mu A$ to 200 $\mu A$. Intraperitoneal (IP) administration of 2-DG at a dose of 250 mg/kg gradually induced an increase in the AD threshold toward 1500 $\mu A$ during a period of about 2-3 weeks of twice daily stimulation, suggesting that the anticonvulsant effect of 2-DG may continue to gradually develop during repeated administration. The gradually increasing anticonvulsant effect on AD threshold was also quite prolonged, as the AD threshold remained elevated for as long as 6 weeks after stopping twice daily 2-DG treatment.

EXAMPLE 2

Effect of 2-DG on Synchronized Bursting in Hippocampal Slices

To further confirm the anticonvulsant effects of 2-DG observed in kindled rats, the effect of 2-DG on synchronized bursting induced by elevation of $[K^+]_o$ in rat hippocampal slices ex corpora was evaluated.

In these experiments, postnatal day 14 to 35 male Sprague-Dawley rats were anesthetized and decapitated. Brains were removed and transferred to ice cold artificial cerebrospinal fluid (ACSF), comprising 124 mM NaCl, 5 mM KCl, 1.25 mM $NaH_2PO_4$, 1.5 mM $MgSO_4$, and 26 mM $NaHCO_3$, supplemented with 10 mM glucose), which was continuously bubbled with 95% $O_2$ and 5% $CO_2$. Transverse hippocampal slices (~400 microns) were prepared on a Leica VT1000s vibratome (Wetzlar Germany). The slices were allowed to recover for 1 hour at room temperature and were then transferred to an interface recording chamber at 34° C. in ACSF with 7.5 mM $[K^+]_o$. Extracellular recordings were made from the CA3 region with an Axioclamp 2B (Axon Instruments, Forest City, Calif.) using a glass microelectrode filled with 150 mM NaCl. Data were recorded and analyzed using PClamp8 (Axon Instruments).

Figure 4:
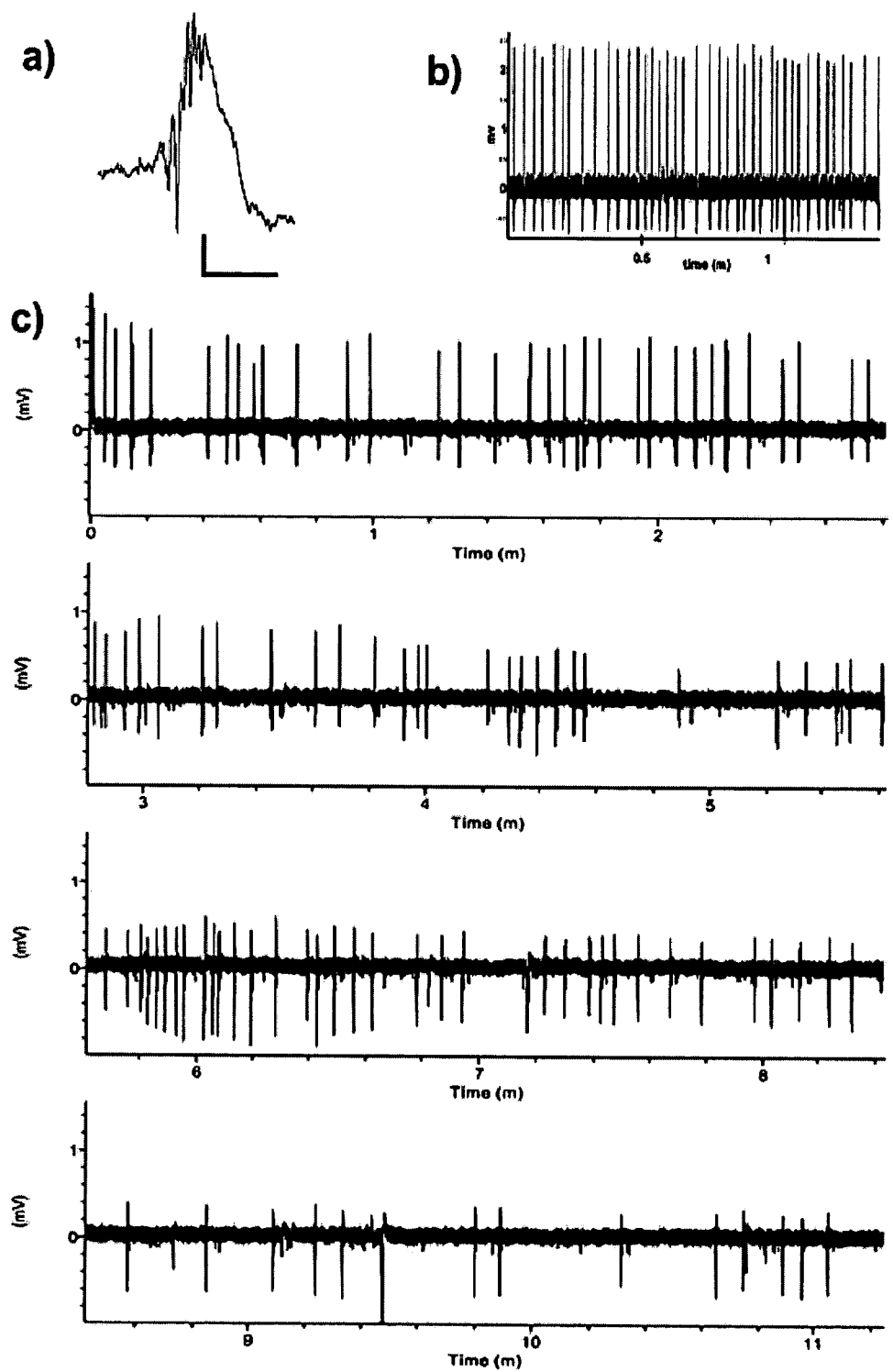
FIGS. 4A through 4C are electrophysiological traces of synchronized spontaneous burst discharges in CA3 induced by increased potassium ($K^+$) ion concentration in rat hippocampal brain slices.

Synchronized bursting was induced by incubating hippocampal slices in ACSF supplemented with to a final concentration of 7.5 mM $[K^+]_o$, Baseline recordings were obtained after exposure to elevated $[K^+]_o$ for 1 hour and the burst frequency had stabilized. The results of these experiments are shown in FIGS. 4A through 4C. The burst frequency decreased progressively after addition of 2-DG as shown in the recordings of FIG. 4B and 4C.

Figure 5A:
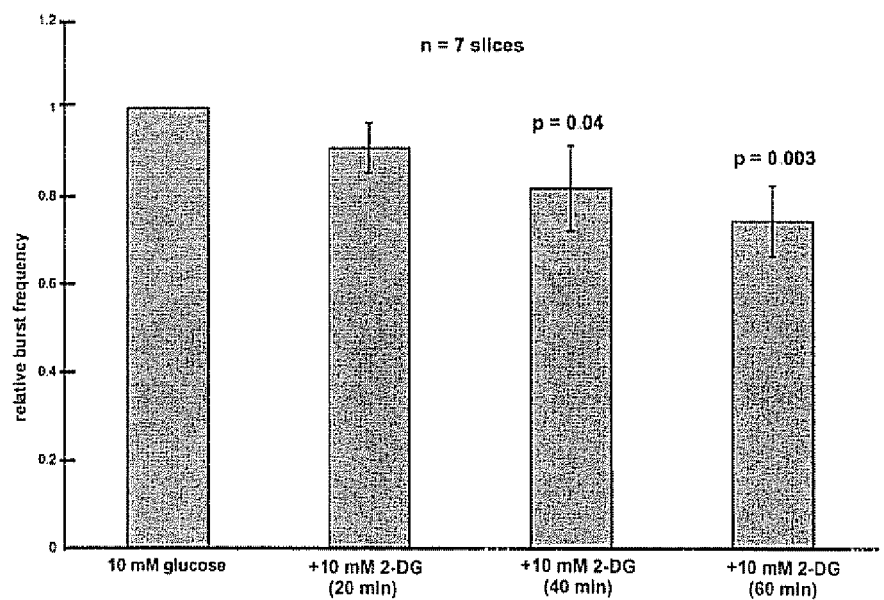
Figure 5B:
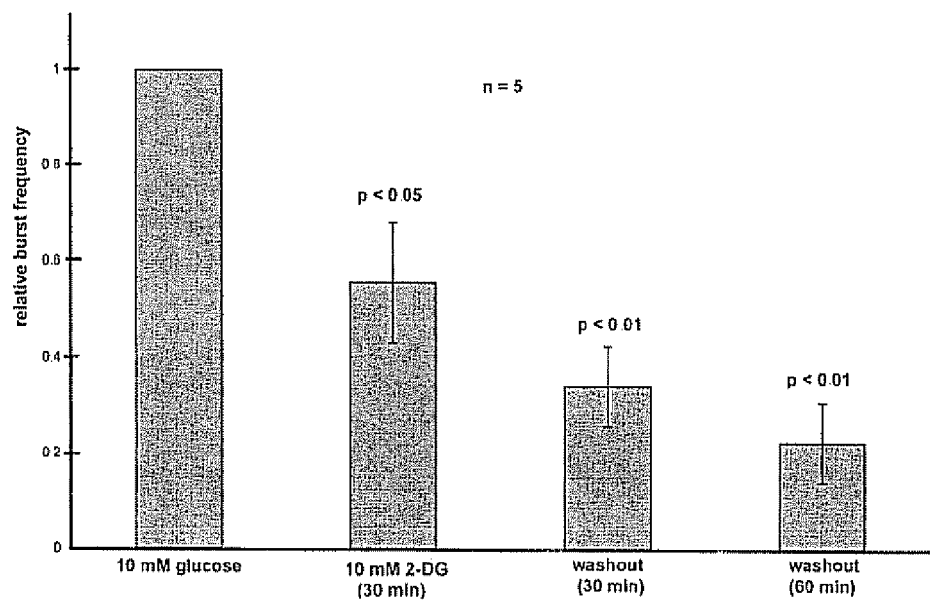
Figure 5C:
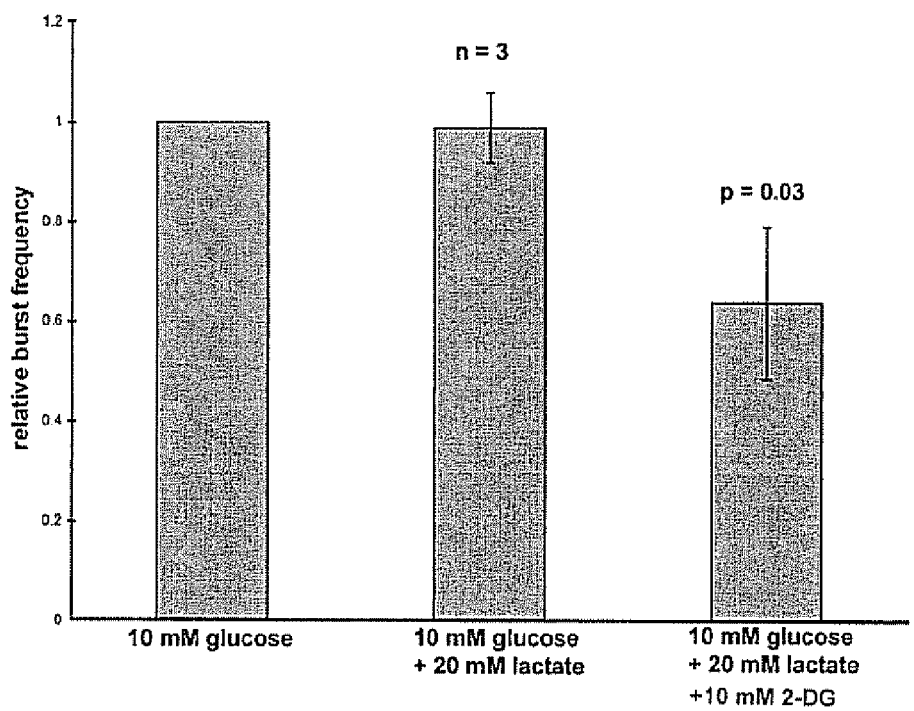

As shown in FIG. 5B, the anticonvulsant effects of 2-DG persisted for as long as 60 minutes after return of the hippocampal slice to ACSF containing 7.5 mM $[K^+]_o$ but no 2-DG. This finding was consistent with previous studies demonstrating that 2-DG is trapped in cells after uptake through the glucose transporter, and 2-DG probably does not wash out of the tissue.

EXAMPLE 3

Reduction of Synchronized Bursting by Iodoacetate

Figure 6:
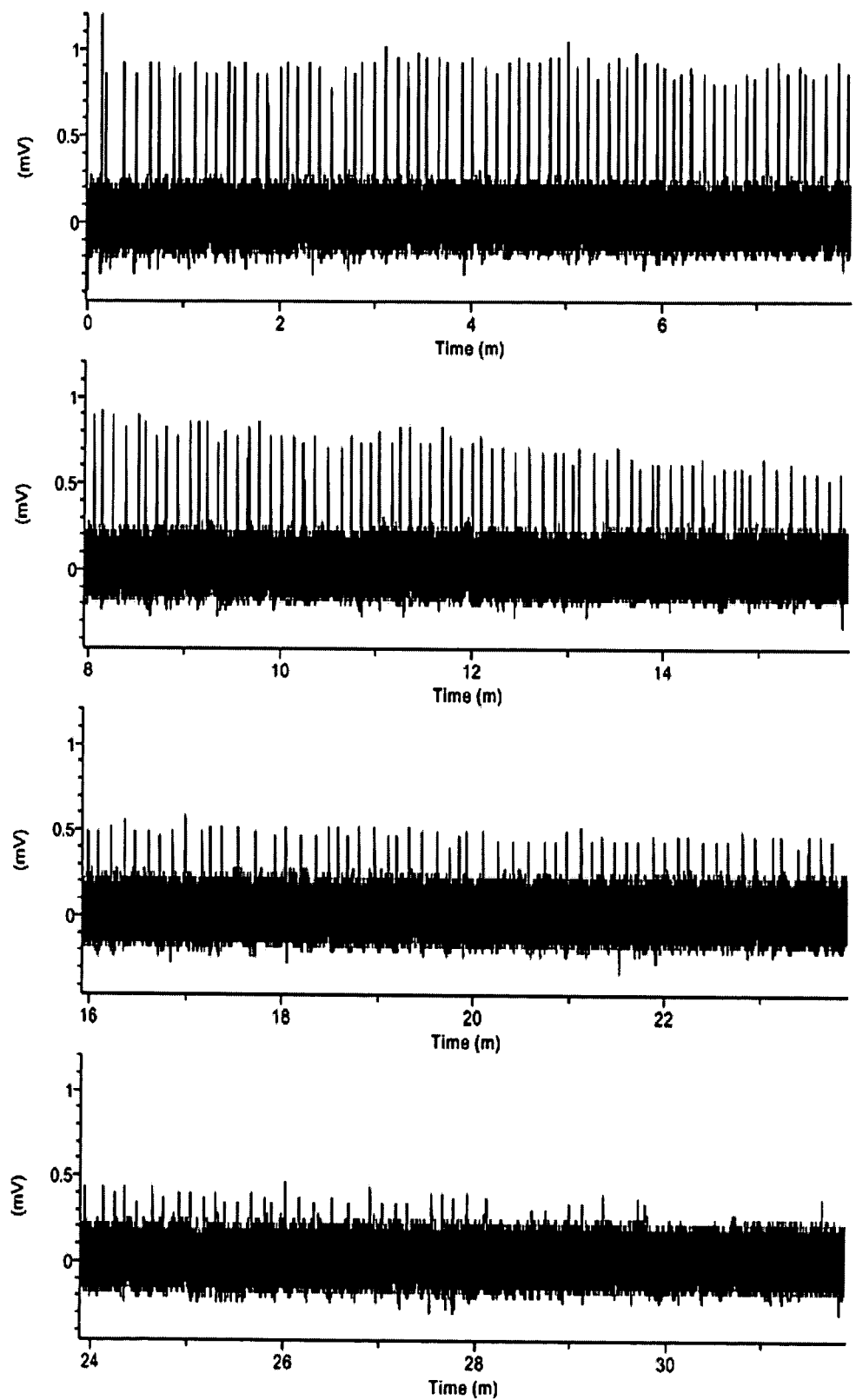
FIG. 6 is an electrophysiological trace of synchronized spontaneous burst discharges in CA3 induced by increased $[K^+]_o$ in rat hippocampal brain slices, and illustrates reduction in epileptic bursts by bath application of iodoacetate.
Figure 7:
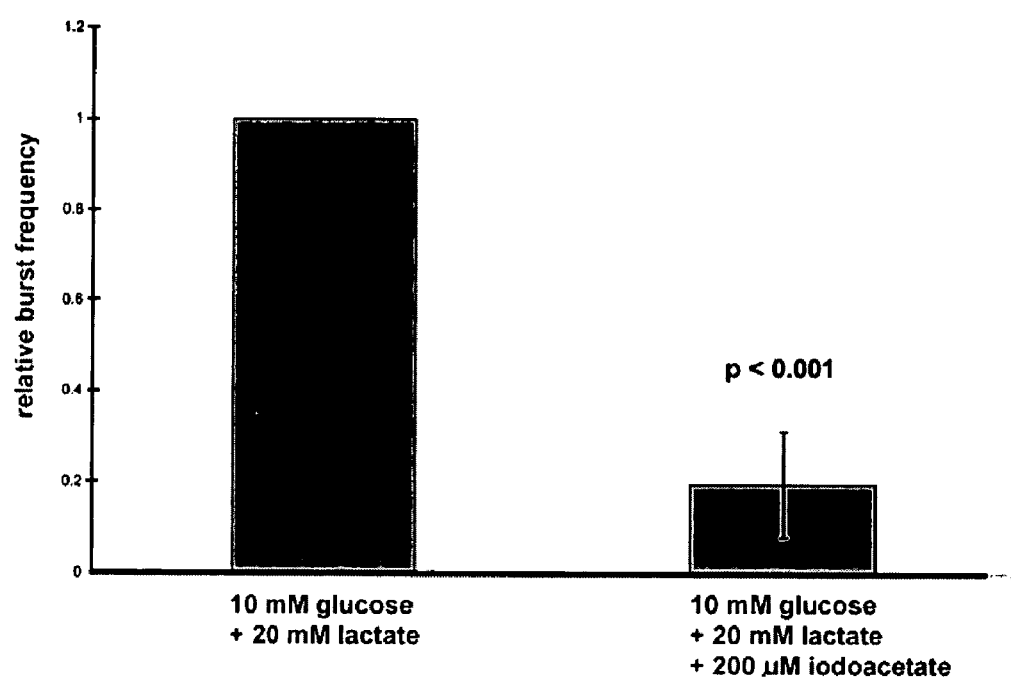
FIG. 7 is a graphical representation demonstrating that the reduction in epileptic bursts by iodoacetate persists when lactate is provided as an alternative cellular energy source.

To confirm that the results set forth above were due to antiglycolytic effects, the experiments set forth in Example 2 were repeated using ACSF supplemented with 10 mM glucose or 10 mM lactate in the presence of 200 uM iodoacetate, an inhibitor of the glycolytic enzyme glyceraldehyde phosphate dehydrogenase (EC 1.2.1.12). The results of these experiments are shown in FIGS. 6 and 7. FIG. 6 shows the rate of baseline synchronized bursting from a hippocampal slice in ACSF with 10 mM $[K^+]_o$, 10 mM glucose, and 20 mM lactate. The reduction in burst frequency is shown in graphical form in FIG. 7. Iodoacetate reduced synchronized bursting, demonstrating that inhibiting glycolysis by glyceraldehyde phosphate dehydrogenase inhibition is also an effective means for reducing neural synchronization, the cellular event associated with various seizure disorders.

EXAMPLE 4

Effect of Energy Source on Induced Synchronized Bursting in Hippocampal Slices To further investigate the anticonvulsant actions of 2-DG, the effects of glucose deprivation on epileptic burst discharges were also evaluated.

Figure 8:
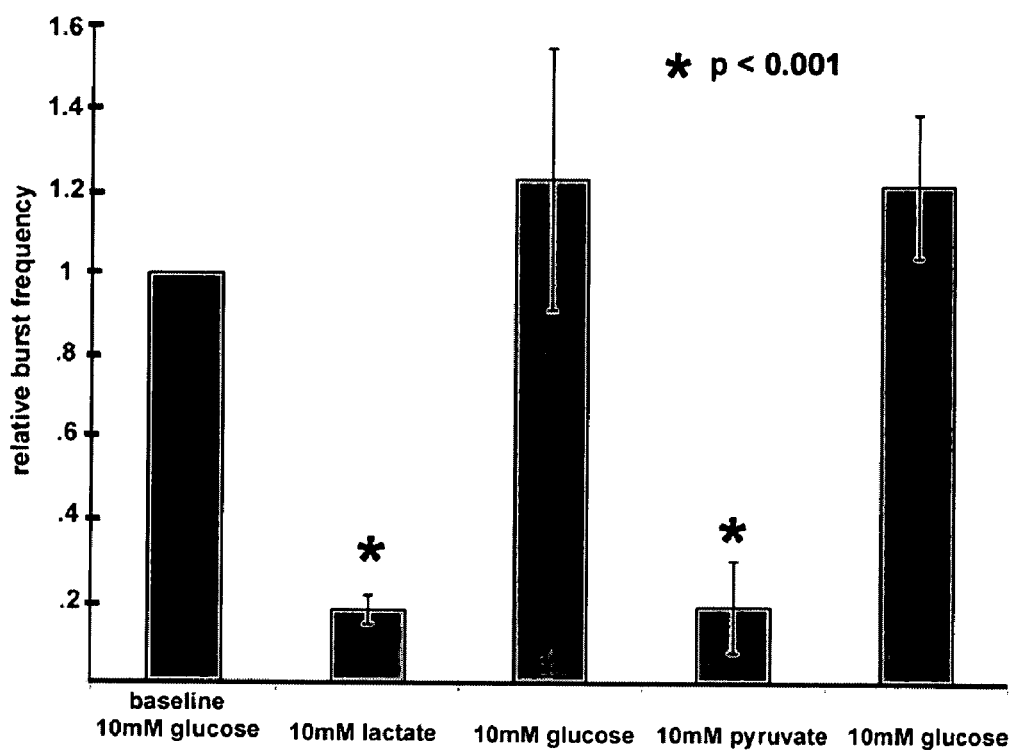
FIG. 8 is a graphical representation demonstrating that removal of glucose and substitution with alternative energy sources such as lactate or pyruvate suppresses synchronized bursts in CA3, which confirms that reducing glycolysis, in this case by removing glucose as a substrate, has anticonvulsant effects.

The effects of glucose deprivation on synchronized burst discharges were examined in rat hippocampal slices ex corpora using the methods described in Example 2. Spontaneous synchronized bursts were recorded in CA3 in ACSF containing 10 mM glucose supplemented with 7.5 mM $[K^+]_o$ for ~1 hr, and then in glucose-free ACSF supplemented with 10 mM lactate or 10 mM pyruvate. The results of these experiments are shown in FIG. 8. The average burst frequency at baseline in 10 mM glucose was found to be regular with an interburst interval of ~3.8 seconds. The interburst interval increased to 24 seconds when the slice was exposed to glucose-free ACSF supplemented with 10 mM lactate, indicating an anticonvulsant effect of glucose deprivation. This effect was rapidly induced and was reversible, with the slowing effect observed within 5-10 minutes, and recovery to baseline values within 10 minutes after return to ACSF containing 10 mM glucose. Similar results were found when glucose was replaced by 10 mM pyruvate. These results demonstrated that removal of glucose and substitution with alternative energy sources such as lactate or pyruvate suppress synchronized bursts in CA3 and have anticonvulsant effects.

EXAMPLE 5

Use of 2-DG to Alleviate Symptoms of Neuropathic Pain in an Animal

The effects of 2-deoxy-D-glucose (2-DG), which has acute anticonvulsant properties in hippocampal slices and prevents the consequences of repeated evoked network synchronization in the kindling model of epilepsy, were evaluated for treatment of neuropathic pain. The effects of 2-DG were examined in the loose sciatic nerve ligation rat model of neuropathic pain. This model exhibits many similarities to the human condition, including mechanical and thermal hyperalgesia and allodynia, which are types of hypersensitivity. Effects of 2-DG on neuropathic pain were assessed by measurement of hindlimb withdrawal latency to mechanical stimulation and development of mechanical allodynia according to standardized methods.

Male Sprague-Dawley rats (Harlan, 250-350 g) were behaviorally tested by measuring hindlimb withdrawal latency in response to mechanical stimulation of the hindlimb with standardized Von Frye filaments of increasing diameter, in order to verify that all animals initially had normal responses prior to surgical procedures and treatments. In the Von Frye method, animals are placed on a wire mesh floor, and the hindlimb is stroked with standardized filaments of increasing diameter until withdrawal is observed. The size of the filament evoking withdrawal is the Von Frye score. Withdrawal to smaller filaments indicates hyperalgesia, or mechanical allodynia when normally innocuous filaments produce withdrawal, and are regarded as measures of pain. Baseline withdrawal scores were used to assess effects of sciatic ligation and treatment with 2-DG.

After obtaining baseline measurements, animals were then anesthetized with a combination of ketamine 70 mg/kg IP and xylazine 7 mg IM. The sciatic nerve was exposed at mid-thigh level by blunt dissection through the biceps femoris muscles. The nerve was freed of adherent tissue, and four ligatures (4.0 chromic gut) were spaced about 1 mm apart. Care was taken to tie the ligatures so that the nerve trunk is just barely constricted when viewed with a dissecting microscope at 40×. This degree of constriction retards, but does not arrest, circulation through the superficial epineural vasculature. The incision was closed in layers, and during the immediate postoperative period the animals were monitored for signs of behavior that would signify unexpected and undesirable reaction to the surgical procedure (loss of weight or appetite, lack of grooming or loss of locomotion).

Figure 9:
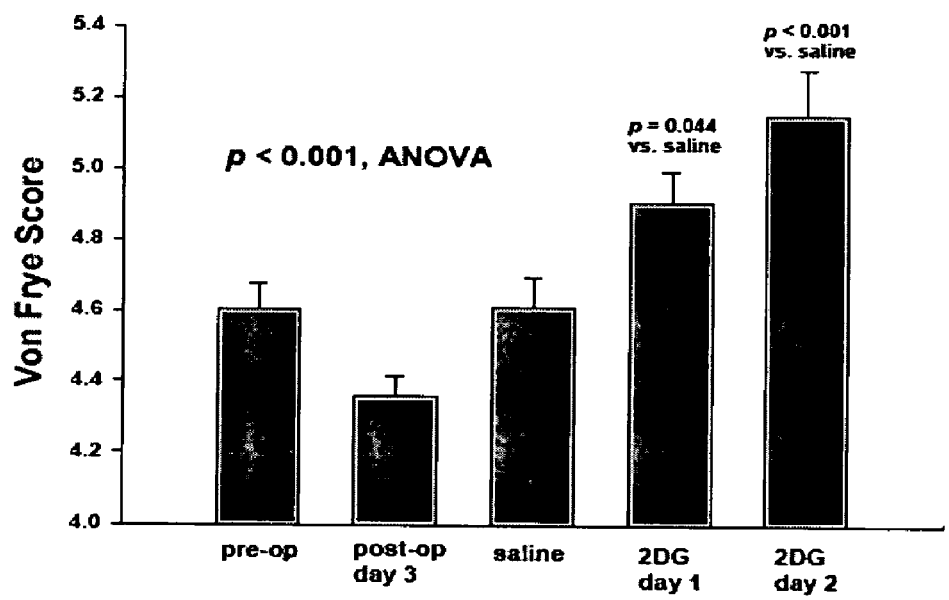
FIG. 9 shows results measuring neuropathic pain using Von Frye filament analysis. Results were statistically analyzed by ANOVA (p=0.037). Saline treatment tended to restore responses toward normal baseline levels, but administration of 2-DG increased Von Frye scores and significantly reduced hyperalgesia compared to saline treatment. The effect of 2-DG diminished after 4 days.

Hindlimb withdrawal responses were assessed postoperatively to verify that mechanical allodynia and hyperalgesia were induced as a result of the surgical ligation. By day 3 after the surgical procedure, animals demonstrated hindlimb withdrawal in response to mechanical stimulation with smaller diameter filaments (lower Von Frye score) that did not evoke withdrawal in baseline testing, indicating development of allodynia (see FIG. 9, p<0.001, ANOVA). Twenty animals with neuropathic withdrawal responses were randomized to receive 2-DG 250 mg/kg IP (n=10) or saline (n=10) at 30 minutes prior to assessment by mechanical stimulation. Treatment with 2-DG acutely reduced mechanical allodynia compared to saline treated controls, as indicated by decreasing sensitivity to mechanical stimulation and increasing Von Frye scores. Treatment with 2-DG did not result in any apparent motor or behavioral impairments. The reduction in sensitivity was observed as early as day 1, and there appeared to be a trend to continued improvement or increasing Von Frye scores on the second day of treatment (see FIG. 9). The differences between saline and 2-DG treated animals were significant at both day 1 of treatment (p=0.044 vs. saline) and day 2 of treatment (p<0.001 vs. saline), and demonstrate that measures of neuropathic pain are reduced by 2-DG. These pain-reducing effects diminished or were extinguished after day 4-5 of administration.

All patents, patent applications, scientific article and other sources and references cited herein are explicitly incorporated by reference herein for the full extent of their teachings as if set forth in their entirety explicitly in this application.

It should be understood that the foregoing disclosure emphasizes certain specific embodiments of the invention and that all modifications or alternatives equivalent thereto are within the spirit and scope of the invention as set forth in the appended claims.

What we claim is:

1. A method for treating epilepsy, in an adult or juvenile human, the method comprising the step of administering to the human an effective amount of 2-deoxyglucose (2-DG).

2. The method of claim 1 for treating an epileptic seizure.

3. The method of claim 2, wherein 2-DG is administered prior to the human having an epileptic seizure.

4. The method of claim 2, wherein 2-DG is administered to the human during an epileptic seizure.

5. The method of claim 2, wherein 2-DG is administered to the human after the human has an epileptic seizure.

6. The method of claim 2, wherein 2-DG is administered within 30 minutes before or 24 hours after the human has an epileptic seizure.

7. A method for reducing or inhibiting epileptic seizures in an adult or juvenile human, the method comprising the step of administering to the human an effective amount of 2-DG.

8. The method of claim 7, wherein 2-DG is administered prior to the human having an epileptic seizure.

9. The method of claim 7, wherein 2-DG is administered to the human during an epileptic seizure.

10. The method of claim 7, wherein 2-DG is administered to the human after the human has an epileptic seizure.

11. The method of claim 7, wherein 2-DG is administered within 30 minutes before or 24 hours after the human has an epileptic seizure.

12. A method for raising the seizure threshold in brain or neural tissue of a human in need thereof, the method comprising the step of administering to the human having epilepsy an effective amount of 2-DG.

13. The method of claim 12 wherein the brain or neural tissue comprise adult or juvenile brain or neural tissue.

14. The method of claim 12, wherein 2-DG is administered prior to the human having an epileptic seizure.

15. The method of claim 12, wherein 2-DG is administered the human having an epileptic seizure.

16. The method of claim 12, wherein 2-DG is administered to the human after the human has an epileptic seizure.

17. The method of claim 12, wherein 2-DG is administered within 30 minutes before or 24 hours after the human has an epileptic seizure.

18. A method for reducing epileptic bursting in human brain cells in a human, the method comprising the step of contacting the cells with an effective amount of 2-DG.

19. The method of claim 18 wherein the human brain cells are adult or juvenile brain cells.

20. The method of claims 18, wherein epileptic bursting is associated with the human animal having an epileptic seizure.

21. The method of claim 20, wherein 2-DG is administered prior to the human having an epileptic seizure.

22. The method of claim 20, wherein 2-DG is administered prior to the human having an epileptic seizure.

23. The method of claim 20, wherein 2-DG is administered to the human after the human has an epileptic seizure.

24. The method of claim 20, wherein 2-DG is administered within 30 minutes before or 24 hours after the human has an epileptic seizure.

25. The method of claim 20 wherein the brain cells are adult or juvenile brain cells.

26. A method of treating epilepsy in a human in need thereof by administering to said human an effective amount of 2-deoxyglucose (2-DG).

27. The method of claim 26, wherein 2-DG is administered to the human within minutes of the onset of epileptic symptoms in the human.

28. The method of claim 26, wherein 2-DG is administered to the human before the onset of epileptic symptoms in the human.

* * * * *